United States Patent [19]

Haber et al.

[11] Patent Number: 5,445,620
[45] Date of Patent: Aug. 29, 1995

[54] DISPOSABLE SAFETY SYRINGE WITH RETRACTABLE SHUTTLE FOR WYETH MEDICATION CARTRIDGE

[75] Inventors: Terry M. Haber, Lake Forest; William H. Smedley, Lake Elsinore; Clark B. Foster, Laguna Niguel, all of Calif.

[73] Assignee: Habley Medical Technology Corp., Laguna Hills, Calif.

[21] Appl. No.: 123,362

[22] Filed: Sep. 17, 1993

[51] Int. Cl.⁶ .............................................. A61M 5/00
[52] U.S. Cl. .................... 604/232; 604/110; 604/198; 604/228
[58] Field of Search ............ 604/110, 192, 195, 197, 604/198, 221, 228, 232, 233, 234, 263

[56] References Cited

U.S. PATENT DOCUMENTS

| | | | |
|---|---|---|---|
| 4,664,654 | 5/1987 | Strauss | 604/198 |
| 4,834,717 | 5/1989 | Haber et al. | 604/232 |
| 4,931,040 | 6/1990 | Haber et al. | 604/110 |
| 4,944,723 | 7/1990 | Haber et al. | |
| 5,045,066 | 9/1991 | Scheuble et al. | 604/198 |
| 5,067,490 | 11/1991 | Haber | |
| 5,084,017 | 1/1992 | Maffetone | 604/228 |
| 5,141,500 | 8/1992 | Hake | 604/198 |
| 5,232,457 | 8/1993 | Grim | 604/197 |

FOREIGN PATENT DOCUMENTS 0467173  1/1992  European Pat. Off. ............ 604/198

*Primary Examiner*—C. Fred Rosenbaum
*Assistant Examiner*—Ronald K. Stright, Jr.
*Attorney, Agent, or Firm*—Townsend and Townsend and Crew

[57] ABSTRACT

A disposable safety syringe has a needle shuttle slidably located within a main syringe barrel. The shuttle has a pair of outwardly extending guide tabs which engage a guide slot formed in the barrel wall. The upper end of the needle shuttle is configured to accept a Wyeth needle cartridge having a needle attached to an ampoule by a carrier. A bushing and rod assembly are mounted in the barrel below the ampoule. After use, the needle shuttle is maneuvered downwardly by the guide tabs to a locking position in which the needle attached to the ampoule is housed within the barrel for safe disposal.

5 Claims, 4 Drawing Sheets

DISPOSABLE SAFETY SYRINGE WITH RETRACTABLE SHUTTLE FOR WYETH MEDICATION CARTRIDGE

BACKGROUND OF THE INVENTION

This invention relates to a relatively low cost, disposable syringe designed to reduce or eliminate accidental needle strikes by enabling selective position control of a cartridge mounted needle from an injecting position to a retracted and locked position.

Hypodermic syringes are used for a variety of injection procedures including the delivery of medicinal drugs and anesthetics to a patient. Once the injection procedure is completed, problems can arise if the syringe is not disposed of properly and adequately. Healthcare workers are susceptible to accidental and potentially infectious needle strikes if the needle is carelessly handled or broken during disposal of the syringe after use. If an accidental needle strike does occur, a blood test is typically required to determine whether the worker has been infected. The cost of performing such tests and the loss of personnel time attendant upon such tests can be particularly damaging to a healthcare facility striving for economy and efficiency.

There are several known syringes designed to provide retraction of a syringe needle after use. In some such designs, the apparatus is designed such that the needle is retracted within the same ampoule which initially housed the medication dispensed with the syringe. In other known devices, the retraction mechanism is designed to retract the used needle within the syringe housing and lock the needle in the retracted position.

While such known designs have been found suitable in a wide variety of applications, none is compatible with a syringe using the Wyeth needle cartridge. In the Wyeth design, a single ended needle is bonded to a plastic carrier member, which in turn is secured to the ampoule containing a liquid medication. The needle passageway is in fluid communication with the interior of the ampoule, and a pliant needle cover, usually fabricated from rubber, is removably attached to the needle carrier member to seal the needle from ambient until the medication is ready to be dispensed. The needle carrier is provided with externally formed threads or ridges. Since the Wyeth needle cartridge provides a convenient supply of a variety of medications at relatively low cost, such cartridges have found wide use. However, after the medication has been dispensed from a Wyeth needle cartridge, the needle is exposed and poses a safety threat requiring special disposal procedures. Consequently, the need exists for an economical disposable syringe which is compatible with the Wyeth type of needle cartridge, and which provides safe handling and disposal for such needle cartridges after use.

SUMMARY OF THE INVENTION

The invention comprises a disposable safety syringe which is designed for use with the Wyeth standard needle cartridge, is relatively simple in design and use, and provides retractable locking for the cartridge after use, with the needle being positioned safely within the syringe barrel.

In the preferred embodiment, the invention includes a main housing having a wall portion with an interior volume, the wall portion having a guide slot with a tab support portion and a tab lock portion.

A needle shuttle dimensioned to be insertable within the interior volume of the main housing has a needle carrier attachment portion and a guide tab locatable in the main housing guide slot. The needle carrier attachment portion is designed to secure an attachable needle and cartridge assembly, preferably a Wyeth type needle and cartridge assembly, and includes an internally threaded end portion preferably formed with threads engageable with an externally threaded portion of the needle carrier.

The needle shuttle guide tab enables manipulation of the needle shuttle between an injection position in which the guide tab is located in the tab support portion of the guide slot and a lock position in which the guide tab is located in the tab lock portion of the guide slot. In the tab support position, the needle shuttle supports an attached needle and cartridge assembly in an extended position: in the tab lock position, the needle shuttle maintains an attached needle and cartridge assembly in a retracted position in which the needle is located within the interior volume of the main housing so that the needle is safety locked in a totally retracted position.

The needle shuttle preferably includes a longitudinally extending wall member terminating in a pair of laterally spaced leg portions each having a guide tab. To facilitate insertion of the needle shuttle within the interior of the main housing, the leg portions are inwardly flexible.

A bushing and rod assembly is dimensioned to be inserted partially within the interior volume of the main housing. The bushing and rod assembly includes means engageable with a slidable piston located within the ampoule for translating the piston towards the dispensing end of the ampoule to expel the contents thereof. The bushing and rod assembly preferably includes a bushing member having a longitudinally extending bore, an outer wall surface of a first diameter and a peripheral portion of a second diameter. The first diameter is smaller than the inner diameter of the interior volume of the main housing, and the second diameter is larger than the inner diameter of the interior volume. The bushing and rod assembly further preferably includes a rod member having an end portion engageable with the ampoule piston. The end portion of the rod member is preferably threaded to engage a threaded portion of the ampoule piston. The bushing member is preferably provided with a longitudinally extending cut-away for enabling the rod member to be press fitted into the bore.

The invention can be configured for shipment with or without the needle and cartridge assembly. When configured for shipment with the needle and cartridge assembly, the assembly is attached to the needle shuttle, and the needle shuttle is positioned by manipulation of the guide tabs to the tab support position in which the needle is extended from the main housing but covered with a removable needle cover. The bushing and rod assembly is installed in the bottom of the main housing, with the rod attached to the ampoule piston. When configured for shipment without the needle and cartridge assembly, the needle shuttle is typically installed in the main housing, and the busing and rod assembly is included with the package.

In use, with the needle and cartridge assembly supported in the main housing in the extended position and the rod member attached to the ampoule piston, the needle cover is removed and the ampoule contents are expelled by forcing the rod member inwardly of the main housing.

After the ampoule contents are expelled, the needle and cartridge assembly are moved to the retracted and locked position by manipulating the needle shuttle by means of the guide tab toward the locking position. The needle carrier, which is attached to the needle shuttle, is automatically withdrawn within the interior of the main housing and locked in place by means of the locking engagement between the needle shuttle guide tab and the tab lock portion of the main housing guide slot.

For a fuller understanding of the nature and advantages of the invention, reference should be had to the ensuing detailed description taken in conjunction with the accompanying drawings.

DESCRIPTION OF THE PREFERRED EMBODIMENT

Figure 1:
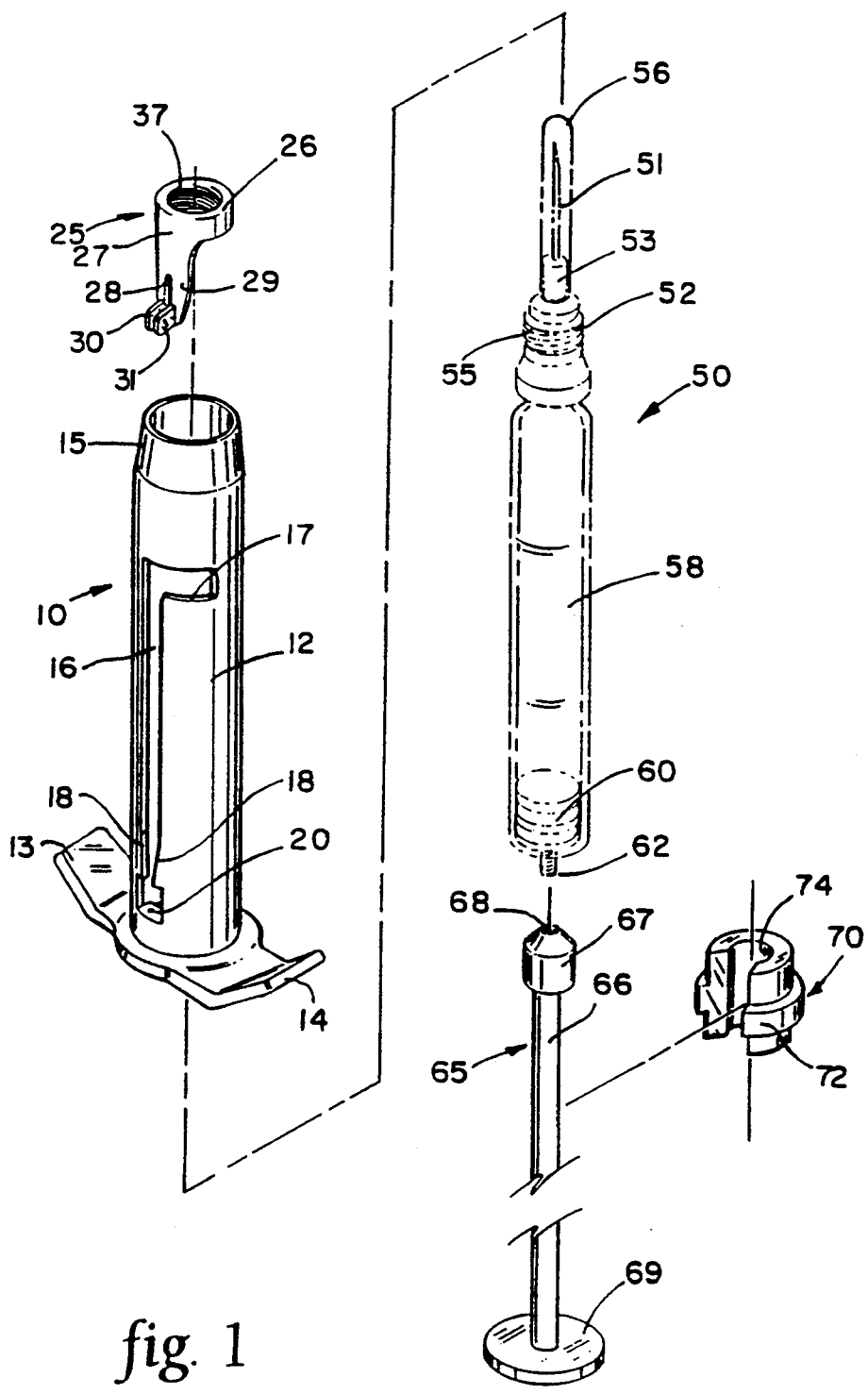
FIG. 1 is a perspective view of a preferred embodiment of the invention.

Turning now to the drawings, FIG. 1 is an exploded perspective view of the preferred embodiment of the invention. As seen in this Fig., the disposable syringe includes a main body member generally designated with reference numeral 10 having a barrel portion 12 with oppositely disposed upwardly extending angled finger tabs 13, 14 integrally formed at the bottom end thereof, and a beveled nose portion 15. Extending longitudinally of barrel portion 12 is a guide slot 16 terminating at the upper end in a laterally extending slot portion 17. Guide slot 16 also has a pair of mutually facing, inwardly tapering wall portions 18 terminating in an enlarged, generally rectangular lock slot portion 20.

A one piece needle shuttle generally designated with reference numeral 25 has a generally cylindrical upper body section 26 and a downwardly depending wall member 27 terminating in a pair of flexible leg portions 28, 29. Leg portions 28, 29 each include one of a pair of outwardly extending guide tab 30, 31 which are laterally spaced by an amount which ensures a locking fit in lock slot 20 in the manner described more fully below.

Figure 2:
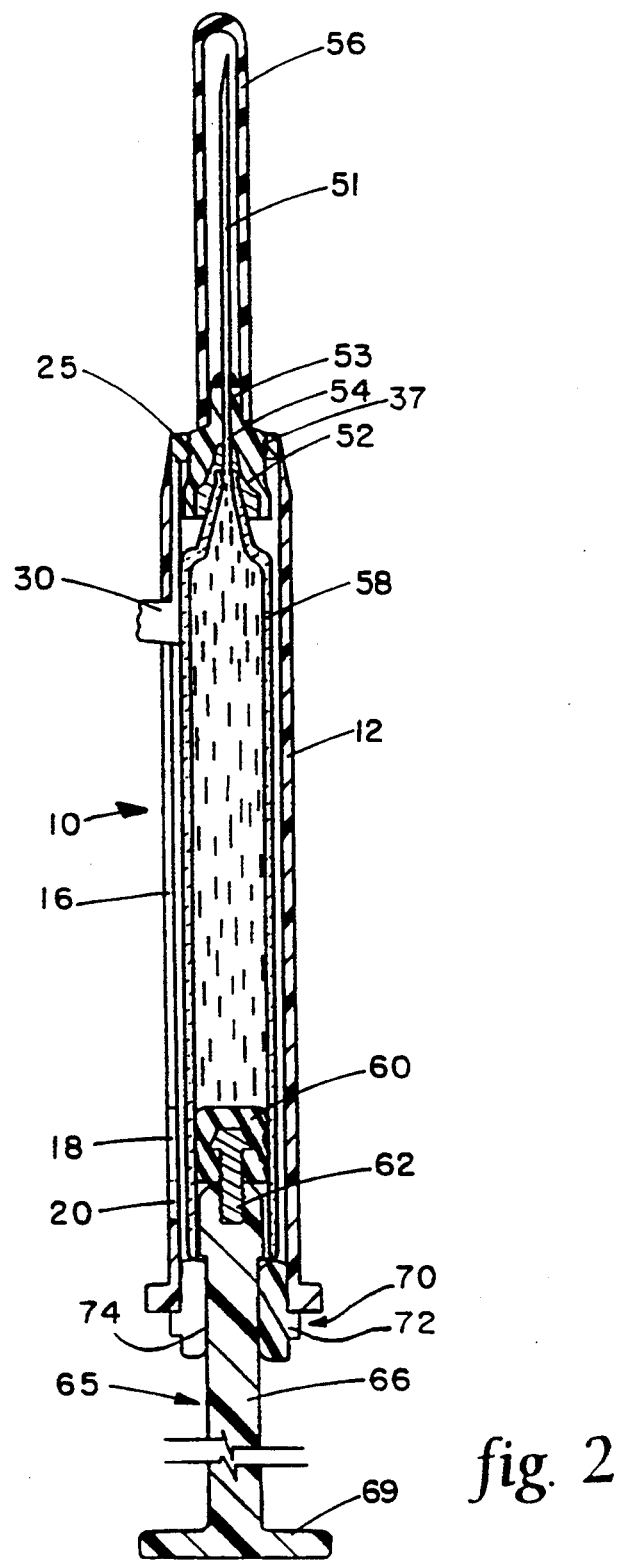
FIG. 2 is a sectional view illustrating the preferred embodiment of the invention prepared for packaging.
Figure 3:
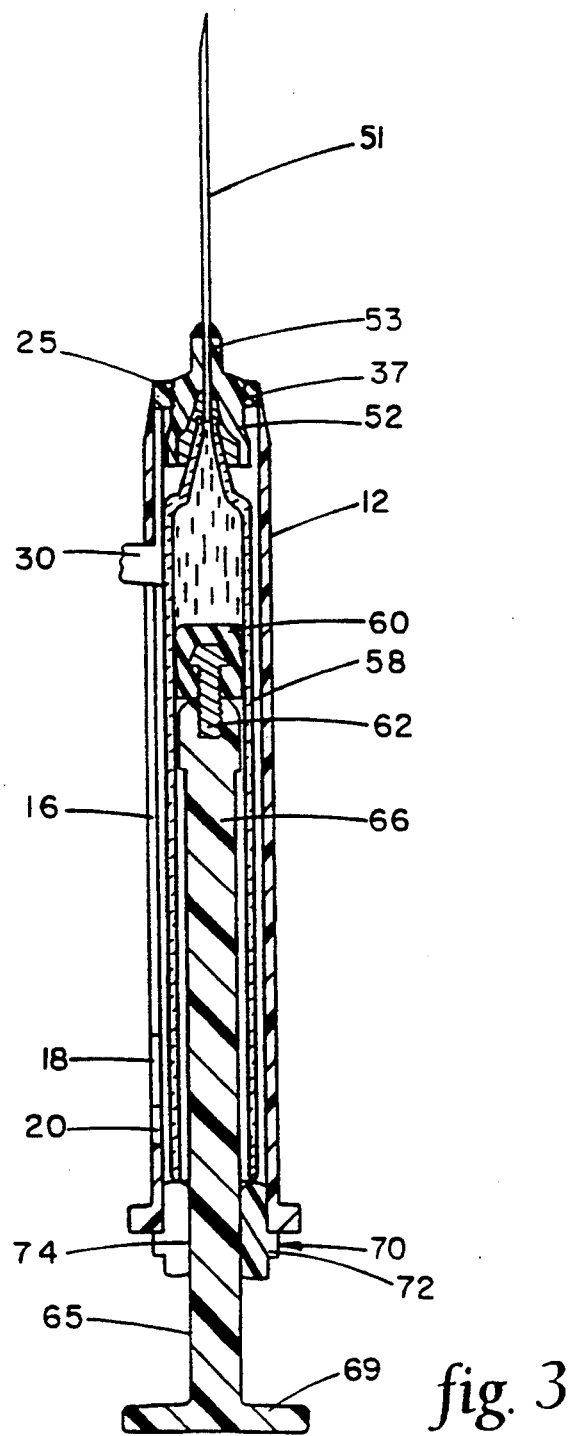
FIG. 3 is a sectional view of the invention during use to expel the medication.

As best seen in FIGS. 1 and 2, the upper body portion 26 of needle shuttle 25 has an internally threaded annular wall portion 37 designed to be threadably engaged with the needle carrier of a standard Wyeth medication cartridge assembly generally designated with reference numeral 50.

More particularly, cartridge assembly 50 includes a single ended needle 51 bonded within a unitary carrier 52. Carrier 52 has a central nose portion 53 and an internal passageway 54 (see FIG. 2), and the lower end of needle 51 is bonded within the passageway 54 typically by means of a suitable adhesive. Needle carrier 52 is normally provided with an external threaded portion 55, and threads 37 formed in the needle shuttle 25 are configured to engage this threaded portion 55.

Again with reference to FIG. 1, the assembly 50 comprising needle 51 and carrier 52 is bonded to a standard Wyeth medicine cartridge or ampoule 58, typically fabricated from glass or pharmaceutically compatible plastic material. A removable needle cover 56 is removably arranged over central nose portion 53 of carrier 52. Cover 56 is typically fabricated from butyl or urethane rubber and seals needle 51, as well as the contents of ampoule 58, from ambient. A sealing piston 60 is located in the bottom interior of ampoule 58 and seals the fluid contents within ampoule 58 prior to dispensing. Piston 60 has a centrally located downwardly depending threaded member 62 configured for threadable engagement with an activation rod generally designated with reference number 65. Rod 65 includes a stem portion 66 with an enlarged upper end 67 having an internally threaded bore 68. The lower end of stem portion 66 terminates in a base portion 69.

A guide bushing generally designated with reference numeral 70 has a generally cylindrical body with an enlarged waist portion 72, and a longitudinally extending central bore 74 dimensioned to receive stem portion 66 of rod 65. To facilitate assembly, a portion of bushing body 70 is cut away so that the stem portion 66 can be pressed into the bore 74. The outer diameter of the body of bushing 70 is dimensioned to provide a close fit in the lower end of the interior of barrel portion 12, while waist portion 72 limits upward movement of bushing 70 within the barrel portion 12.

In use, the device is assembled in the following fashion. Needle shuttle 25 is inserted into the bore of barrel 12 from below and manipulated upwardly. Leg portions 28, 29 are flexed inwardly in order to permit locking tabs 30, 31 to clear the first portion of the inner wall of barrel 12. Shuttle 25 is manipulated further upwardly within barrel 12 until the locking tabs 30, 31 extend through the guide slot 16 in barrel 12. Thereafter, shuttle 25 can be manipulated upwardly by means of the protruding guide tabs 30, 31 until the shuttle 25 is in the uppermost position at which the upper edges of the guide tabs 30, 31 encounter the upper edge of the slot portion 17. Thereafter, shuttle 25 is rotated by means of the guide tabs 30, 31 into the slot portion 17 so that the shuttle is supported by the lower edge of slot portion 17. If the syringe is to be shipped with the cartridge assembly 50, the assembly 50 is now inserted via the bottom opening in barrel 12 and maneuvered upwardly therein until the threaded portion 55 of carrier 52 can be engaged with the internal threaded portion 37 of shuttle 25. Ampoule 58 is now supported within barrel 12 in the attitude illustrated in FIG. 2. The stem portion 66 of rod 65 is pressed fitted into bushing 70 and is threadably attached to piston member 62 by rotating rod 65 in the proper direction. Bushing 70 is fitted into the interior of barrel portion 12. This shipping configuration for the invention is illustrated in FIG. 2. In some applications, the end user will supply the cartridge 50: in such applications, the two subassemblies comprising the body member 10/shuttle 25, and the rod 65/bushing 70 are shipped in the package to the user.

When the syringe is scheduled to be used for an injection, the needle cover 56 is first removed. The user then applies an upward force to rod 65. This causes piston 60 within ampoule 58 to be translated upwardly and expel the contents of ampoule 58 via passageway 54 and needle 51.

After the contents of ampoule 58 has been expelled by the required amount, rod 65 is disengaged from piston 60, and rod 65 and bushing 70 are manually withdrawn through the bottom opening in barrel portion 12.

Figure 4:
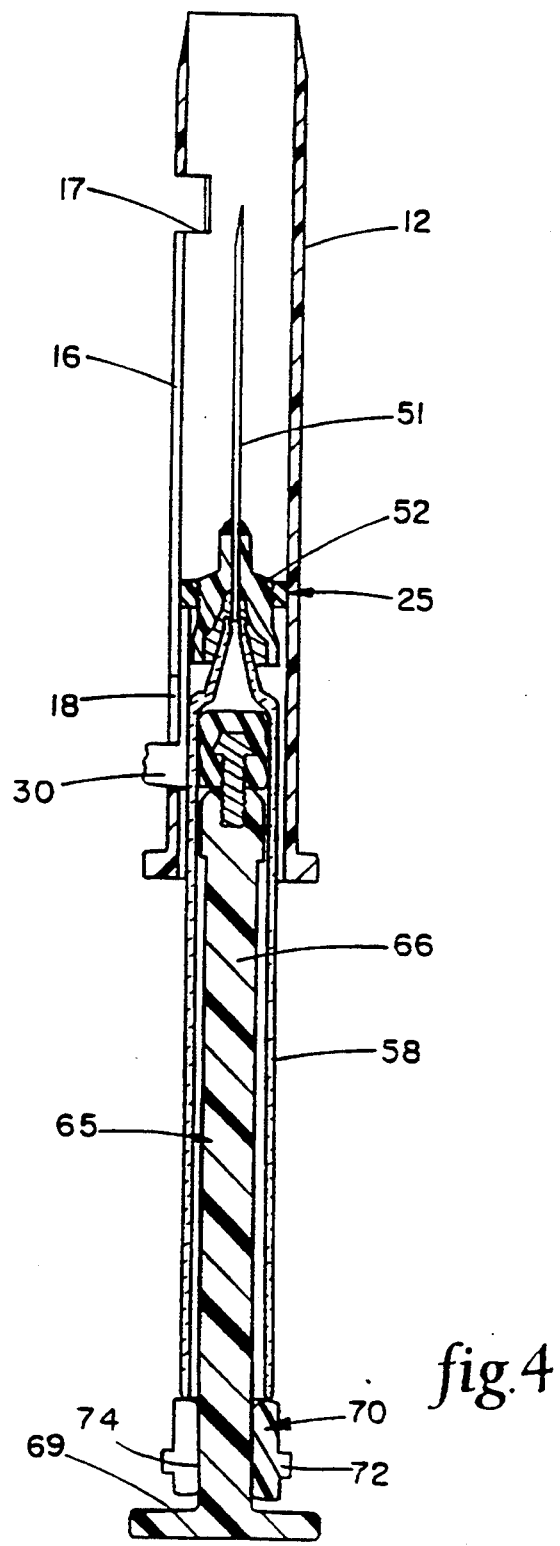
FIG. 4 is a sectional view of the invention in condition for disposal and illustrating the needle in the retracted locked position.

Thereafter, needle shuttle 25 is rotated by rotating guide tabs 30, 31 to the guide slot 16 and needle shuttle 25 is manipulated downwardly until the guide tabs 30, 31 are engaged in the lock slot 20. As the needle shuttle 25 is manipulated downwardly, the cartridge assembly 50 follows this motion and needle 51 is withdrawn into the interior of barrel 12 until the position illustrated in FIG. 4 is achieved. As seen in this FIG., the needle 51 is locked in place entirely within the barrel 12 illustrated in FIG. 4 and the spent assembly may now be disposed of in a safe manner.

As will now be apparent, disposable syringes fabricated according to the teachings of the invention are completely compatible with standard Wyeth cartridge assemblies, and provide a safe and economical technique for disposing of used assemblies of this type. In addition, due to the simplicity of the design of the invention, the ampoule 58 may be readily inserted by the user in those applications in which it is not desired to transmit the ampoule 58 along with the syringe supplied to the user.

While the above provides a full and complete disclosure of the preferred embodiment of the invention, various modifications, alternate constructions and equivalents may be employed as desired. For example, although expressly designed for use with Wyeth type cartridge assemblies, the device can be adapted for use with any other type of standard or custom designed cartridge in which the needle is bonded to the ampoule using a carrier capable of interlocking engagement with a needle shuttle. Further, although needle shuttle 25 has been illustrated and described as having internal threads 37 designed for threaded engagement with external threads 55, shuttle 25 may be configured to provide a snap fit or a friction fit to the needle carrier 52, if desired. Therefore, the above description should not be construed as limiting the scope of the invention, which is defined by the appended claims.

What is claimed is:

1. A combination disposable syringe and cartridge assembly, the cartridge assembly including an ampoule and a needle carrier secured to the ampoule, the ampoule having a main body portion, a dispensing end and an opposite end, a piston housed within the main body for expelling the contents of the ampoule, said combination comprising:

a main housing having a wall portion with an interior volume, said wall portion having a guide slot with a tab support portion and a tab lock portion;

a needle shuttle having a needle carrier attachment portion and a guide tab engageable in said guide slot;

said needle shuttle supporting an attached needle assembly in a first extended position when the needle shuttle guide tab is located in the tab support portion of said guide slot and maintaining an attached needle assembly within said interior volume of said main housing when the needle shuttle guide tab is located in the tab lock portion of said guide slot, the needle shuttle guide tab including:

a pair of axially extending, circumferentially flexible leg portions; and a laterally spaced, radially extending tab portion formed on each of said flexible leg portions;

a bushing and rod assembly insertable in said interior volume of said main housing and including:

means for translating the ampoule piston towards the dispensing end of the ampoule to expel the contents; and a rod member having an end portion engageable with the ampoule piston;

said bushing and rod assembly including a rod-member-guiding bushing member having a longitudinally extending bore, an outer wall surface of a first diameter and a peripheral portion of a second diameter, said first diameter being smaller than the inner diameter of said interior volume, said second diameter being larger than said inner diameter of said interior volume; and said bushing member being provided with a longitudinally extending cut-away for enabling said rod member to be laterally press-fitted into said bore.

2. The invention of claim 1 wherein said needle carrier attachment portion of said needle shuttle includes an internally threaded end portion.

3. The invention of claim 2 wherein the cartridge assembly comprises a needle carrier having an externally threaded portion; and wherein said internally threaded end portion of said needle shuttle is formed with threads matched to the externally threaded portion of said needle carrier.

4. The invention of claim 1 wherein said guide slot includes an inwardly tapering wall portion, adjacent the tab lock portion, engageable with the circumferentially flexible leg portions.

5. The invention of claim 1 wherein the ampoule piston has a threaded portion; and wherein said rod member end is threadably engageable with said threaded portion.

* * * * *